United States Patent [19]

Flagg

[11] 4,216,316
[45] Aug. 5, 1980

[54] PROCESS FOR THE PRODUCTION OF ALKYL CYANATES AND OLIGOMERS

[75] Inventor: Edward E. Flagg, Midland, Mich.

[73] Assignee: The Dow Chemical Company, Midland, Mich.

[21] Appl. No.: 10,298

[22] Filed: Feb. 8, 1979

[51] Int. Cl.$^2$ .................. C07C 118/00; C07C 122/00; C07D 251/34
[52] U.S. Cl. .............................. 544/193; 260/429 R; 260/453 AL; 260/453 AR; 260/453 P; 544/221; 544/222
[58] Field of Search ................... 260/453 P; 544/193, 544/222, 221

[56] References Cited

U.S. PATENT DOCUMENTS 3,553,244  1/1971  Grigat et al. ..................... 260/453 P

OTHER PUBLICATIONS

Kauer et al., J. Am. Chem. Soc., vol. 86, pp. 4732-4733 (1964).
Jensen, et al., Acta. Chem. Scand., vol. 20, 2091 at 2096 (1966).

*Primary Examiner*—Dolph H. Torrence
*Attorney, Agent, or Firm*—Douglas N. Deline

[57] ABSTRACT

A process is disclosed for the preparation of alkyl cyanates, alkyl isocyanurates, multifunctional alkyl cyanates, and oligomers of multifunctional alkyl isocyanates by reacting cyanogen halide with the corresponding thallium(I) salt of an alkanol at reduced temperatures, optionally in the presence of an inert solvent. Subsequently, warming the resulting product to ambient temperature causes isomerization to the corresponding aliphatic isocyanate and ultimately oligomerization to form trialkyl isocyanurate or oligomers of multifunctional alkyl isocyanates.

17 Claims, No Drawings

PROCESS FOR THE PRODUCTION OF ALKYL CYANATES AND OLIGOMERS

BACKGROUND OF THE INVENTION

The invention comprises a novel method to produce alkyl cyanates, isocyanates, isocyanurates, and similar multifunctional cyanates, isocyanates and oligomers of multifunctional isocyanates.

A simple process for producing alkyl cyanates by reacting a metal alkoxide with cyanogen halide has been sought since at least 1895 when Hantzsch and Mai reported in Berichte, 28, 2466 (1895) that the reaction produced instead nearly quantitative yields of diethyl imidocarbonate.

Known methods of producing and isolating alkyl cyanates include the preparation of 5-alkoxyl-1,2,3,4-thiatriazoles followed by thermal decomposition according to the following graphic representation:

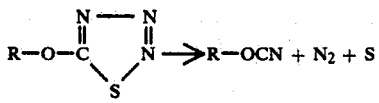

This is the only known general method to prepare alkyl cyanates. However, it is a multistep reaction and the literature cautions that 5-alkoxyl-1,2,3,4-thiatriazole will explode if not handled carefully. Alternatively, one may prepare O-methyl-N-hydroxythiocarbamates which thermally decompose according to the following reaction:

The difficulty with this method is in the separation of the alkyl cyanate before further reaction occurs with other products of the decomposition. Loudas et al. in U.S. Pat. No. 3,733,349 and Grigat et al. in U.S. Pat. No. 3,553,244 disclose a method for producing certain halogenated alkyl cyanates, aryl cyanates, or aliphatic cyanates containing electron withdrawing substituents by the reaction between an alcohol, base and cyanogen chloride. The method is not generally applicable to use with unsubstituted alkyl hydroxy compounds since under such conditions the cyanogen chloride will react preferentially with the base. Finally it is known that certain aliphatic alcohols react successively with sodium hydride or butyl lithium and then with cyanogen chloride to produce cyanates. This known reaction has been used only for producing certain complex sterically hindered cyanates that were incapable of spontaneous isomerization. The three known products

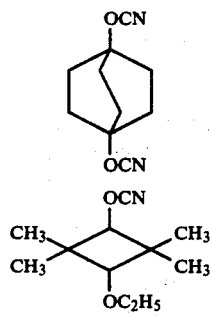

and $(CH_3)_3CCH_2OCN$, required the use of unusual aliphatic moieties and expensive bases.

SUMMARY OF THE INVENTION

The invention is a process for preparing alkyl cyanates, alkyl isocyanates, alkyl isocyanurates or multifunctional alkyl cyanates, multifunctional alkyl isocyanates and oligomers of multifunctional alkyl isocyanates comprising reacting cyanogen halide with thallium(I) alkoxide or the thallium(I) salt of a glycol, multifunctional alkanol, or substituted alkanol at reduced temperatures. By use of the terms halogen or halogenated wherever they occur hereinafter, reference is made to fluorine, chlorine, bromine and iodine.

The immediate product is the corresponding alkyl cyanate, or multifunctional alkyl cyanate. This alkyl cyanate or multifunctional alkyl cyanate may be isolated and preserved without isomerization occurring. Alternatively the cyanate may be allowed to spontaneously isomerize at an elevated temperature to form the corresponding alkyl isocyanate, or multifunctional alkyl isocyanate. Further retention of the alkyl isocyanate or multifunctional isocyanate at such higher temperature produces the alkyl isocyanate oligomer.

The invention is suitable for use in producing common straight chain alkyl dicyanates or multifunctional cyanates, their isomers, and oligomers in addition to a wide variety of alkyl monocyanates, their isomers, and oligomers. The alkyl cyanates, multifunctional cyanates, isocyanates and oligomers formed by this process are useful for the formation of resins, polymers, and for use as polymerization cross-linking agents.

DETAILED DESCRIPTION OF THE INVENTION

Thallium(I) salts of alkanols, substituted alkanols or other organic compounds containing hydroxy radicals attached to alkyl moieties are one reactant for use in this process. Such salts are conveniently prepared by alkoxide exchange with the easier to prepare thallium(I) ethoxide according to well-known laboratory procedures.

These thallium(I) salts are produced from alkanols of the general formula

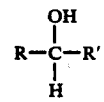

wherein R is a radical having 20 carbons or less selected from a group consisting or aryl, alkyl, halogenated alkyl, alkoxy, polyalkoxy, hydroxy substituted alkyl, hydroxy substituted alkoxy, and hydroxy substituted polyalkoxy; and R' is a radical having 20 carbons or less selected from a group consisting of hydrogen, aryl, alkyl, halogenated alkyl, alkoxy, polyalkoxy, hydroxy substituted alkyl, hydroxy substituted alkoxy and hydroxy substituted polyhydroxy.

Examples of such thallium(I) salts that may be used in the practice of this invention include but are not necessarily limited to: thallium(I) methoxide, thallium(I) ethoxide, thallium(I) phenyl methoxide, thallium(I) 2,2,2-trihaloethoxide, the thallium(I) salts of halogenated alkoxides, the thallium(I) salts of aryl substituted alkoxides, dithallium(I) 1,6-hexanedioxide, the dithallium(I) salt of all glycols of the formula $HO(CH_2)_nOH$ wherein n is an integer from 2 to 20, the dithallium(I) salt of polymers of the formula $HOCH_2(OCH_2CH_2)_nOH$ wherein n is an integer from 1 to 9, the dithallium(I) salt of polymers of the formula $CH_3CH(OH)CH_2-O-[CH_2CH(CH_3)O]_nH$ wherein n is an integer from 1 to 6, the dithallium(I) salt of polymers of the formula $HOCH_2CH_2(OCH_2CH_2)_nOH$ wherein n is an integer from 1 to 9, trithallium(I) 1,2,3-propane trioxide, etc.

The second reactant is a cyanogen halide. The preferred second reactant is cyanogen chloride. This reactant may be added to the reaction in a stoichiometric ratio as determined by the functionality of the thallium (I) alkoxide reactant or in an excess. In one embodiment of this invention cyanogen halide is used as the solvent. In this embodiment large excesses of cyanogen halide may be used.

It is also possible to use less than a stoichiometric amount of cyanogen halide particularly if the thallium(I) alkoxide reactant has a low solubility in the solvent chosen for the reaction. Preferred is a mole ratio of cyanogen halide to thallium(I) alkoxide of at least 0.9.

Common unreactive organic solvents may also be used as the solvent for the reaction. Suitable unreactive organic solvents include aprotic polar solvents and simple aliphatic solvents. Diethyl ether and other low molecular weight alkyl ethers are examples of preferred unreactive organic solvents. Most preferred are ethers having 10 carbon atoms or less.

The reaction may be carried out at temperatures from about $-60°$ C. to about $+75°$ C. The reaction should preferably occur at reduced temperatures of less than about 25° C. if the alkyl cyanate product is to be isolated. Most preferred are temperatures less than 0° C. At elevated temperatures isomerization and oligomerization occur resulting first in the production of the corresponding isocyanate compound and then oligomers of the isocyanate compound. Isomerization and oligomerization may conveniently be stopped at any time by cooling the compound.

The temperature at which the cyanate compounds spontaneously isomerize is different depending on the aliphatic or aryl moieties present in the compound. Likewise the temperature at which spontaneous oligomerization occurs varies depending on the aliphatic or aryl moieties present in the compound. The relevant temperature in each case may easily be determined by ordinary experimental techniques.

The reaction is carried out in any suitable reaction vessel capable of retaining the reactants, solvents and products. Elevated pressures are not necessary but may be employed if desired as for example to aid in dissolution of one or more of the reactants.

DESCRIPTION OF SPECIFIC EMBODIMENTS OF THE INVENTION

Having described the invention the following examples are included as illustrative and not to be considered as limiting.

EXAMPLE I

Preparation of Ethyl Cyanate, Ethyl Isocyanate and Ethyl Isocyanurate

Thallium(I) ethoxide ($TlOC_2H_5$, 32.8 g) was placed in a dropping funnel with 45 ml of diethyl ether solvent and connected to one opening of a 500 ml three-necked flask. Cyanogen chloride (ClCN, 9.4 g) was combined with 150 ml of diethyl ether in the 500 ml flask equipped with the dropping funnel containing the thallium ethoxide solution. A dry ice reflux trap and mechanical stirrer were added. The flask and cyanogen chloride solution were cooled to about $-40°$ C. and the thallium ethoxide/ether solution was added. A white precipitate formed immediately upon addition.

After addition of the thallium ethoxide/ether solution the temperature was raised to about 0° C. and maintained at about 0° C. for 1.5 hours with stirring. The solution was filtered and the white precipitate collected. The precipitate was dried with $N_2$ gas and found to weigh 32.6 g. Subsequent analysis by X-ray diffraction confirmed the precipitate to be substantially pure thallium chloride. Conversion based on thallium chloride produced approached 100 percent.

The filtered ether solution was stored for about approximately 16 hours at a temperature of about $-14°$ C. It was filtered again using anhydrous $Na_2SO_4$ and glass wool. Residual cyanogen chloride and ether were removed by fractionation at 0° C. and a pressure of 100 torr. leaving a colorless liquid. Chemical analysis by ordinary techniques of oxidation analysis and infrared absorption spectroscopy were consistent with ethyl cyanate formation.

The isomerization of the resulting product was identified by warming the flask and contents to ambient temperature; about 25° C. After a few minutes a reaction was observed. Both increase in pressure and a significant exotherm occurred. After about two and one-half hours analysis of the resulting mixture by infrared spectroscopy and nuclear magnetic resonance spectroscopy confirmed the presence of both ethyl cyanate and ethyl isocyanate. Quantities of both ethyl cyanate and ethyl isocyanate were isolated by distillation. Both products oligomerized to form the trimer ethyl isocyanurate when left at ambient temperature, about 25° C., over an extended time period.

EXAMPLE II

Preparation of Benzyl Cyanate, Benzyl Isocyanate and Benzyl Isocyanurate

Thallium(I) phenyl methoxide was prepared by alkoxide exchange by the reaction at a temperature of at least 90° C. between thallium(I) ethoxide and phenyl methanol. The thallium(I) phenyl methoxide was dissolved in diethyl ether and added over a short period of time to a quantity of cyanogen chloride and diethyl ether in a 500 ml three-necked flask accompanied by stirring. The temperature was maintained at or below about 0° C. until reaction was completed. After filtration and distillation chemical analysis of the product indicated cyanate formation had occurred.

The product was less stable at ambient temperature then ethyl cyanate and rearranged rapidly to form benzyl isocyanate. The product solidified on isomerization indicating oligomerization also had occurred. Further analysis by conventional methods confirmed the existence of benzyl and isocyanate moieties.

EXAMPLE III 2,2,2-Trifluoroethyl Cyanate

The thallium(I) salt of 2,2,2-trifluoroethanol was prepared according to common laboratory procedures and added to diethyl ether for addition in the same manner as with previous examples. Reaction with cyanogen chloride at temperatures less than 0° C. was not complete; however, some 2,2,2-trifluoroethyl cyanate was formed and identified according to well-known techniques of chemical analysis.

EXAMPLE IV

Preparation of 1,6-Hexamethylene Dicyanate, 1,6-Hexamethylene Diisocyanate and Oligomers Dithallium(I) 1,6-hexanedioxide was prepared by a normal alkoxide exchange reaction and added to a solution of diethyl ether and cyanogen chloride in a 500 ml three-necked flask. The dithallium(I) 1,6-hexanedioxide was not itself substantially soluble in diethyl ether. After reaction at temperatures less than about 25° C., the solvent was evaporated and a small quantity of viscous liquid isolated. Ordinary chemical methods of oxidation analysis and spectrographic analysis by nuclear magnetic resonance spectroscopy and infrared absorption spectroscopy confirmed 1,6-hexamethylene dicyanate had been produced followed by rearrangement into 1,6-hexamethylene diisocyanate and oligomer formation.

I claim:

1. A process for the production of organic cyanate compounds comprising reacting a cyanogen halide compound with the thallium(I) salt of a second compound of the formula

wherein R is a radical having 20 carbons or less selected from a group consisting of aryl, alkyl, halogenated alkyl, alkoxy, polyalkoxy, hydroxy substituted alkyl, hydroxy substituted alkoxy, and hydroxy substituted polyalkoxy; and R' is a radical having 20 carbons or less selected from a group consisting of hydrogen, aryl, alkyl, halogenated alkyl, alkoxy, polyalkoxy, hydroxy substituted alkyl, hydroxy substituted alkoxy and hydroxy substituted polyhydroxy at a temperature less than the temperature at which the organic cyanate compound isomerizes to the corresponding isocyanate compound, and recovering the organic cyanate compound formed.

2. The process of claim 1 wherein the second compound is ethanol.

3. The process of claim 1 wherein the second compound is phenylmethanol.

4. The process of claim 1 wherein the second compound is 2,2,2-trihalo ethanol.

5. The process of claim 2 wherein the second compound is 1,6-hexanediol.

6. The process of claim 1 wherein the reaction occurs in a solvent that is a low molecular weight alkyl ether containing 20 carbon atoms or less.

7. The process of claim 6 wherein the solvent is diethyl ether.

8. The process of claim 1 wherein the cyanogen halide is cyanogen chloride.

9. A process for the production of trimers of organic isocyanate compounds comprising reacting a cyanogen halide compound with the thallium(I) salt of a second compound of the formula

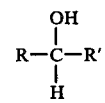

wherein R is a radical having 20 carbons or less selected from a group consisting of aryl, alkyl, halogenated alkyl, alkoxy, polyalkoxy, hydroxy substituted alkyl, hydroxy substituted alkoxy, and hydroxy substituted polyalkoxy; and R' is a radical having 20 carbons or less selected from a group consisting of hydrogen, aryl, alkyl, halogenated alkyl, alkoxy, polyalkoxy, hydroxy substituted alkyl, hydroxy substituted alkoxy, and hydroxy substituted polyhydroxy at a temperature at which the organic cyanate compound formed isomerizes to the corresponding isocyanate compound and oligomerizes.

10. A process for the production of oligomers of organic isocyanate compounds comprising reacting a cyanogen halide compound with the thallium(I) salt of a second compound of the formula

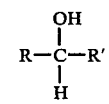

wherein R is a radical having 20 carbons or less selected from a group consisting of aryl, alkyl, halogenated alkyl, alkoxy, polyalkoxy, hydroxy substituted alkyl, hydroxy substituted alkoxy, and hydroxy substituted polyalkoxy; and R' is a radical having 20 carbons or less selected from a group consisting of hydrogen, aryl, alkyl, halogenated alkyl, alkoxy, polyalkoxy, hydroxy substituted alkyl, hydroxy substituted alkoxy, and hydroxy substituted polyhydroxy at a temperature less than the temperature at which the organic cyanate compound isomerizes to the corresponding isocyanate compound, recovering the organic cyanate compound formed and retaining said compound at an elevated temperature at which the organic cyanate compound formed isomerizes to the corresponding isocyanate compound and oligomerizes to form an isocyanurate compound.

11. The process of claim 9 or 10 wherein the second compound is ethanol.

12. The process of claim 9 or 10 wherein the second compound is phenylmethanol.

13. The process of claim 9 or 10 wherein the second compound is 2,2,2-trihalo ethanol.

14. The process of claim 9 or 10 wherein the second compound is 1,6-hexanediol.

15. The process of claim 9 or 10 wherein the reaction occurs in a solvent that is a low molecular weight alkyl ether containing 20 carbon atoms or less.

16. The process of claim 9 or 10 wherein the solvent is diethyl ether.

17. The process of claim 9 or 10 wherein the cyanogen halide is cyanogen chloride.

* * * * *